(12) United States Patent
Vaders et al.

(10) Patent No.: US 11,040,189 B2
(45) Date of Patent: Jun. 22, 2021

(54) ELECTRODE ASSEMBLIES WITH ELECTRICALLY INSULATIVE ELECTRODE SPACERS, AND RELATED DEVICES, SYSTEMS, AND METHODS

(71) Applicant: Intuitive Surgical Operations, Inc., Sunnyvale, CA (US)

(72) Inventors: Dennis H. Vaders, West Haven, CT (US); Adam Ross, Prospect, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 542 days.

(21) Appl. No.: 15/800,248

(22) Filed: Nov. 1, 2017

(65) Prior Publication Data

US 2018/0126149 A1 May 10, 2018

Related U.S. Application Data

(60) Provisional application No. 62/417,561, filed on Nov. 4, 2016.

(51) Int. Cl.
*A61B 18/14* (2006.01)
*A61B 18/00* (2006.01)
(Continued)

(52) U.S. Cl.
CPC ............... *A61N 1/04* (2013.01); *A61B 18/14* (2013.01); *A61B 18/1445* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS 5,891,142 A * 4/1999 Eggers ............... A61B 18/1442
606/51
8,361,071 B2 1/2013 Tetzlaff et al.
(Continued)

OTHER PUBLICATIONS

Schlick, Christopher M., Industrial Engineering and Ergonomics Visions, Concepts, Methods and Tools, 2009, Springer, pp. 595-608 (Year: 2009).*

(Continued)

*Primary Examiner* — Linda C Dvorak
*Assistant Examiner* — Annabeth E Rodriguez
(74) *Attorney, Agent, or Firm* — Jones Robb, PLLC

(57) ABSTRACT

An electrode assembly may include an electrode support made of a first electrically insulative material and an electrode on the electrode support, the electrode having a working surface extending generally transverse to a thickness of the electrode. The electrode assembly may further include an insulative spacer retained in the electrode and made of a second electrically insulative material. The second electrically insulative material may be different from the first electrically insulative material. The insulative spacer of the electrode assembly may have a body portion extending into the thickness of the electrode, and a head portion protruding beyond the working surface of the electrode.

21 Claims, 11 Drawing Sheets

(51) Int. Cl.
  *A61N 1/04*     (2006.01)
  *A61N 1/05*     (2006.01)
  *A61B 34/30*    (2016.01)
  *A61B 17/00*    (2006.01)

(52) U.S. Cl.
  CPC ....... *A61B 34/30* (2016.02); *A61B 2017/0088* (2013.01); *A61B 2018/00083* (2013.01); *A61B 2018/00136* (2013.01); *A61B 2018/00148* (2013.01); *A61B 2018/00404* (2013.01); *A61B 2018/00589* (2013.01); *A61B 2018/00607* (2013.01); *A61B 2018/1405* (2013.01); *A61B 2018/1455* (2013.01); *A61N 1/05* (2013.01)

(58) Field of Classification Search
  CPC ...... A61B 2018/145; A61B 2018/1452; A61B 2018/1455; A61B 2018/1457; A61B 2018/146; A61B 2018/1462; A61F 2002/30968
  See application file for complete search history.

(56) References Cited

U.S. PATENT DOCUMENTS

| | | | |
|---|---|---|---|
| 8,858,547 | B2 | 10/2014 | Brogna |
| 8,939,975 | B2* | 1/2015 | Twomey ............ A61B 18/1442 606/52 |
| 9,055,961 | B2 | 6/2015 | Manzo et al. |
| 2004/0122423 | A1* | 6/2004 | Dycus ................ A61B 18/1482 606/51 |
| 2013/0325031 | A1 | 12/2013 | Schena et al. |
| 2013/0325033 | A1 | 12/2013 | Schena et al. |
| 2017/0196618 | A1* | 7/2017 | Scholer .................. A61B 18/14 |
| 2017/0238990 | A1* | 8/2017 | Soni ................... A61B 18/1445 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

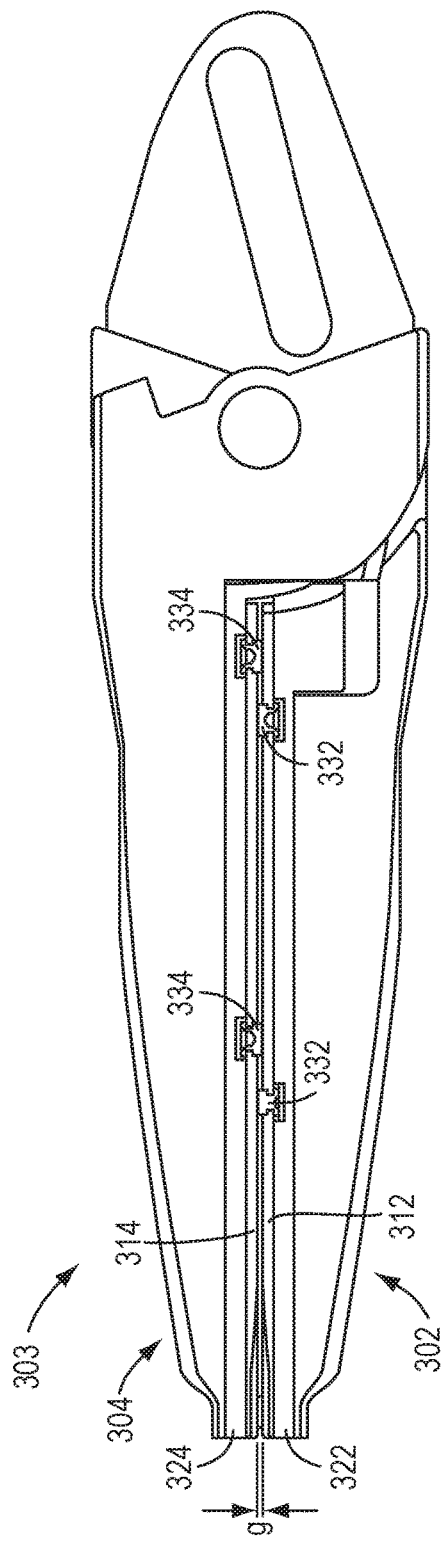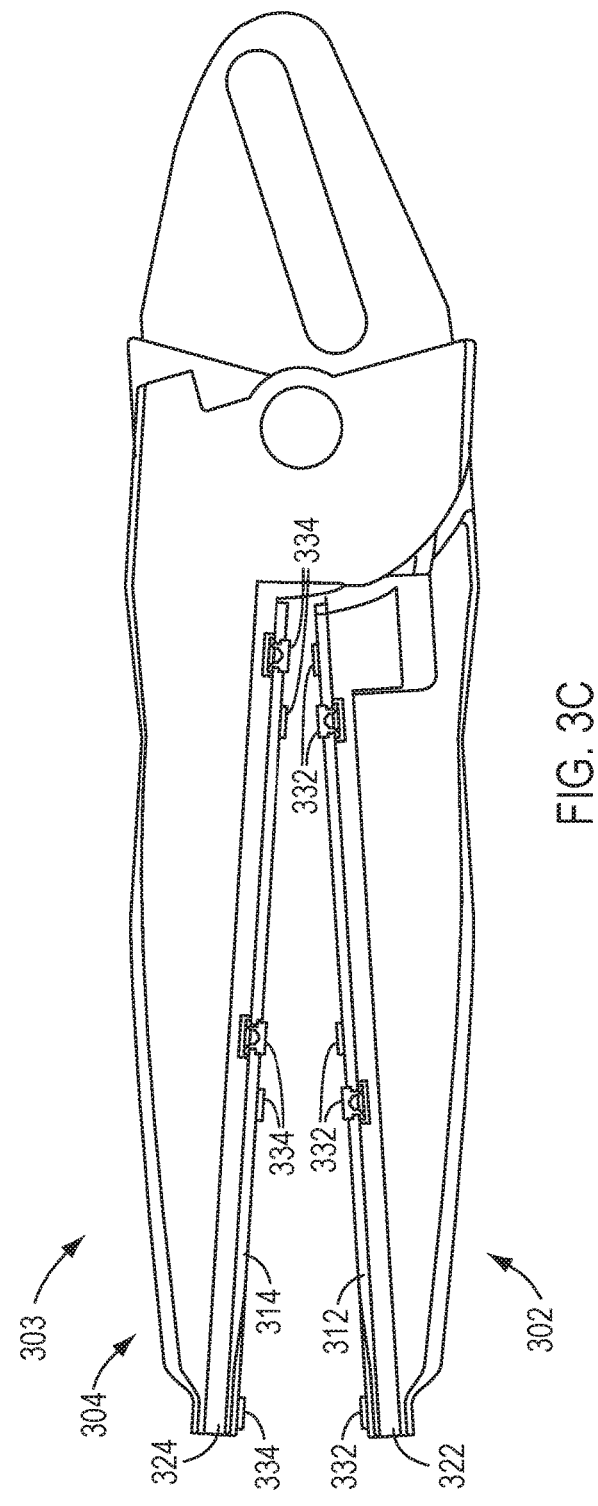

ELECTRODE ASSEMBLIES WITH ELECTRICALLY INSULATIVE ELECTRODE SPACERS, AND RELATED DEVICES, SYSTEMS, AND METHODS

RELATED APPLICATIONS

This application claims priority to Provisional U.S. Patent Application No. 62/417,561, filed on Nov. 4, 2016, which is incorporated by reference herein in its entirety.

This application is related to U.S. patent application Ser. No. 15/800,252, filed on even date herewith, which claims priority to Provisional U.S. Patent Application No. 62/417,567, entitled "ELECTRICALLY INSULATIVE ELECTRODE SPACERS, AND RELATED DEVICES, SYSTEMS, AND METHODS," filed on Nov. 4, 2016, the entire contents of which are incorporated by reference herein.

TECHNICAL FIELD

The present disclosure relates generally to electrically insulative spacers used to separate opposing electrode assemblies. More specifically, the present disclosure relates to electrically insulative spacers and electrode assemblies for electrical flux delivery instruments, such as, for example, electrosurgical instruments, and related systems and methods.

INTRODUCTION

An electrical flux delivery instrument can have various configurations. In some configurations, an electrical flux delivery instrument has two separated electrodes configured as parts of opposing jaw members that are operably coupled to grip material between the electrodes. In operation, an electrical flux delivery instrument treats the material layers sandwiched by the electrodes by passing energy between the electrodes so as to heat-fuse (e.g., seal) the material layers. Generally, one or more spacers made from insulative material are used to maintain a requisite degree of separation (i.e., a gap) between a surface of an electrode and an opposing surface, such as the surface of an opposing electrode. Where the opposing surface is a surface of the other electrode, such spacers can prevent a short circuit by impeding (e.g., preventing) the electrode surfaces from being driven into mutual contact. Spacers can also prevent undesirable electrical arcing by keeping surfaces of opposing electrodes sufficiently spaced from one another.

In the context of the electrical flux delivery instrument being an electrosurgical instrument, energy, such as, for example, bipolar energy, passed between electrodes is used to deliver electrical energy so as to fuse or cauterize tissue. Tissue or other body parts can be gripped between two electrodes of an end effector at the distal end of an electrosurgical instrument, and electrosurgical energy can be passed between the electrodes in order to fuse or otherwise heat-treat the grasped tissue. An example of such tissue fusing includes fusing together opposing walls of a blood vessel. In this way, the blood vessel can be fused closed, resulting in a sealing of the vessel at the fused region. Surgical instruments that perform this action are often referred to as sealing instruments (e.g., a "vessel sealer"). Such electrosurgical instruments also can be used, for example, for cold-cutting, tissue dissection, coagulation of tissue bundles generally (e.g., other than for sealing), and tissue manipulation/retraction. Once tissues, such as, for example, those of a blood vessel, are fused together, the fused region can be cut without any resulting bleeding.

An end effector of an electrical flux delivery instrument can include a pair of opposing jaw members pivotably coupled together to open and close so as to clamp or otherwise retain a material (e.g. tissues) through which energy will be passed. Accordingly, one of a pair of opposing electrodes provided as part of each of the pair of opposing jaw members, respectively. Generally, the opposing electrodes themselves have a proximal end and a distal end, with proximal generally being in a direction closest to the location where the jaw members are pivotably coupled to each other.

There is a continued need to improve upon spacers used to maintain a distance between opposing electrodes so as to provide robust spacer mechanisms that facilitate manufacturing, are durable, and/or have a configuration that allows for a relatively large exposed area of the electrode surfaces. In particular, there is a need for spacer mechanisms that facilitate manufacturing of electrode assemblies that have spacers made of durable material.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, the present disclosure contemplates an electrode assembly. The electrode assembly has an electrode support made of a first electrically insulative material and an electrode on the electrode support, the electrode having a working surface extending generally transverse to a thickness of the electrode. The electrode assembly further has an insulative spacer retained in the electrode and made of a second electrically insulative material, the second electrically insulative material being different from the first electrically insulative material. The insulative spacer of the electrode assembly has a body portion extending into the thickness of the electrode, and a head portion protruding beyond the working surface of the electrode.

In accordance with another aspect of the present disclosure, a method for making an electrode assembly is disclosed. The method can include providing an electrode with an opening extending into a thickness of the electrode, and inserting an electrically insulative spacer comprising a body portion and a head portion in the opening such that at least part of the body portion is positioned in the opening and the head portion is positioned to overlie an exposed working surface of the electrode, wherein the electrically insulative spacer is made of metal or ceramic. The method can further include retaining the inserted electrically insulative spacer in the opening via a mechanical interlocking of the spacer and the electrode.

In accordance with yet another aspect of the present disclosure, an electrosurgical instrument comprising a shaft and an end effector. The end effector can be operably coupled to the shaft, and the end effector has a pair of opposing jaw members, each jaw member comprising an electrode assembly disposed to face the electrode assembly the opposing jaw member. The electrode assembly has an electrode support made of a first electrically insulative material, and an electrode on the electrode support, the electrode having a working surface extending generally transverse to a thickness of the electrode. The electrode assembly further has an insulative spacer retained in the electrode and made of a second electrically insulative material, the second electrically insulative material being different from the first electrically insulative material. The insulative spacer comprises a body portion extending into the thickness of the electrode, and a head portion protruding beyond the working surface of the electrode.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 3B is a longitudinal cross-sectional view of the end effector of FIG. 3A with the jaw members in a closed position.

FIG. 3C is a longitudinal cross-sectional view of the end effector of FIG. 3A with the jaw members in an open position.

Figure 1:
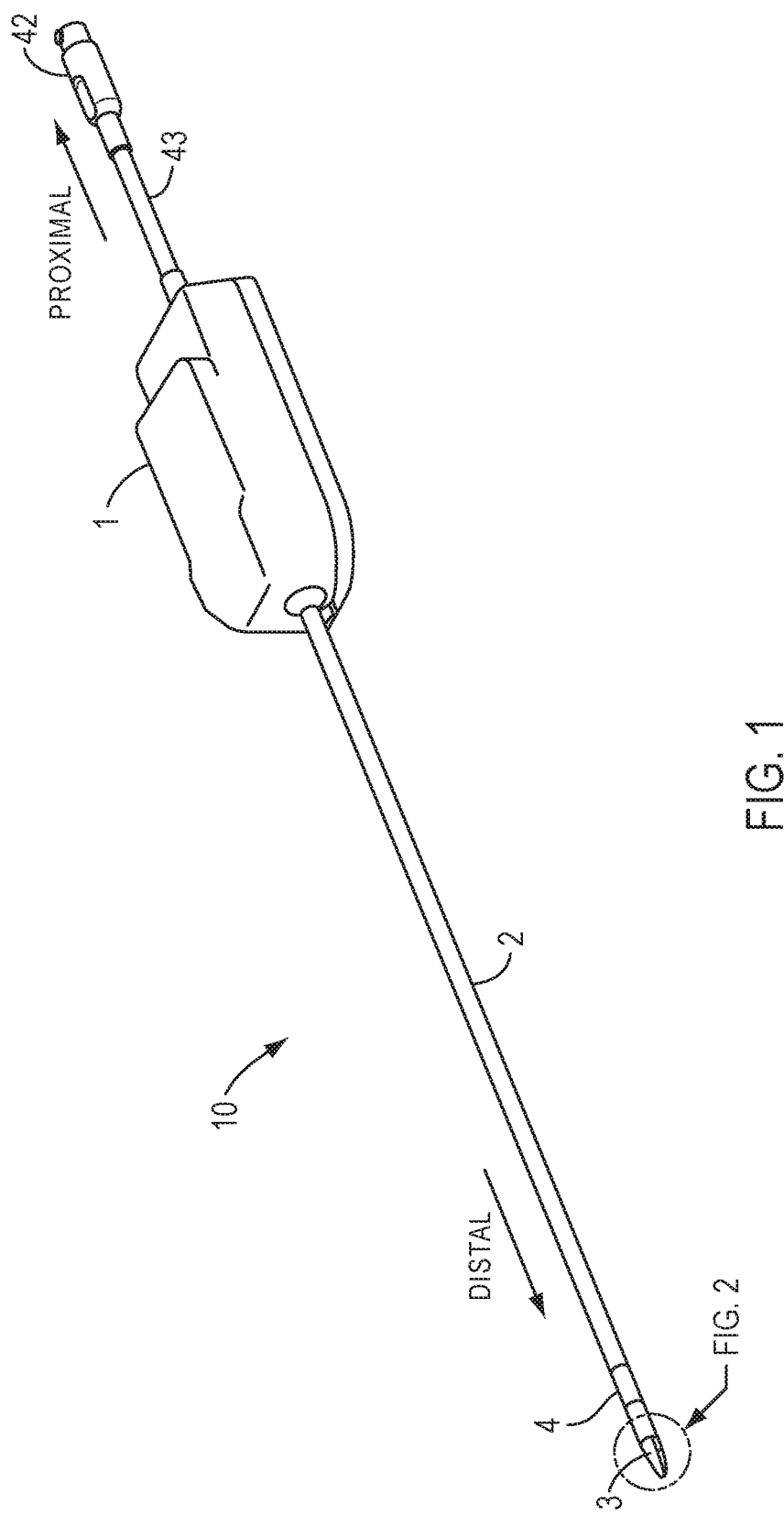
FIG. 1 is a diagrammatic perspective view of a minimally invasive surgical instrument in accordance with an exemplary embodiment of the present disclosure.

Although the following detailed description makes reference to exemplary illustrative embodiments, many alternatives, modifications, and variations thereof will be apparent to those skilled in the art and are contemplated as within the scope of the present disclosure and claims. Accordingly, it is intended that the claimed subject matter is provided its full breadth of scope, including encompassing equivalents.

DESCRIPTION OF EXEMPLARY EMBODIMENTS

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. In the orientation of the figures in the application, relative proximal and distal directions of the devices have been labeled.

The present disclosure contemplates electrode assemblies, and electrical flux delivery instruments including the same, having one or more insulative electrode spacers. In addition, the present disclosure contemplates systems and methods related to electrode assemblies having one or more insulative electrode spacers, as well as electrical flux delivery instruments including the same.

Electrode spacers of an electrode assembly according to exemplary embodiments of the present disclosure may be fitted or otherwise restrained in an opening of an electrode of the electrode assembly such that a working surface of the electrode spacer protrudes slightly beyond the exposed surface of the electrode. Accordingly, when opposing electrodes are brought together to clamp or grip material therebetween, the protruding electrode spacers keep the electrodes spaced apart by a gap that corresponds to the extent each spacer protrudes. Furthermore, electrode spacers according to exemplary embodiments of the present disclosure are made of insulative material(s), which prevents a short circuit and undesirable electrical arcing by impeding (e.g., preventing) the electrode surfaces made of conductive material from being driven into mutual contact and sufficiently spaced from one another.

Electrode assemblies in accordance with various exemplary embodiments of the present disclosure may be designed to be long-lasting and resistant to damage or failure. To provide such durability, the insulative electrode spacers of an electrode assembly in accordance with various exemplary embodiments of the present disclosure may be made of relatively high strength material, such as, for example, metal or ceramic.

To make a metal electrode spacer as disclosed herein sufficiently electrically insulative, for example to prevent shorting and arcing as discussed above, various exemplary embodiments contemplate hard anodizing at least a portion of the metal spacer. In various exemplary embodiments in accordance with the present disclosure, a sufficiently insulative hard anodized electrode spacer has a dielectric strength of at least 200 V/mil (i.e., volts per 0.001 inch). In various other exemplary embodiments in accordance with the present disclosure, a sufficiently insulative hard anodized electrode spacer has a dielectric strength of at least 1000 V/mil (i.e., volts per 0.001 inch). A person of ordinary skill in the art would understand that the dielectric strength of a hard anodized electrode spacer in accordance with the present disclosure will vary in accordance with the type of instrument in which the electrode spacer is to be incorporated.

A metallic, hard anodized electrode spacer as disclosed herein, may be made from aluminum, zirconium, titanium, magnesium, or alloys thereof. Moreover, although the present disclosure contemplates the use of hard anodized metal electrode spacers, any material upon which an oxide layer can be formed may be hard anodized and used as an electrode spacer in accordance with the present disclosure.

A ceramic electrode spacer as disclosed herein is inherently sufficiently insulative, while also being sufficiently durable. For example, various exemplary embodiments of ceramic electrode spacers may have a dielectric strength of at least 150 V/mil. A ceramic insulative electrode spacer may be made from various ceramic materials, including, for example, zirconium oxide, aluminum oxide, titanium oxide, or combinations thereof.

Regardless of the material of the electrode spacer, a person having ordinary skill in the art would understand that, at a minimum, the electrode spacer should have a dielectric strength that is greater than the quotient of the voltage to be applied across the electrodes over the thickness of the electrode spacer that spans between the electrodes. For example, if 100 volts are being applied across the electrodes, and the thickness of the electrode spacer spanning between the electrodes is 0.010 inches, then the dielectric strength of the spacer must be greater than 100 V/0.010 inches, which is equal to 10 V/mil, in order to be an effective insulator.

Electrodes of an electrode assembly in accordance with various exemplary embodiments of the present disclosure may be made of conductive materials, such as, for example, metal(s) or metal injection molded material(s), such as, for example, stainless steel, zirconium, titanium, or combinations thereof.

In various exemplary embodiments of an electrode assembly, one or more insulative spacers (e.g., metallic, hard anodized spacers or ceramic spacers) may be incorporated into the thickness of an electrode made of metal. For example, various exemplary embodiments contemplate forming electrode assemblies in accordance with the present disclosure by metal injection molding the electrode with openings in the electrode body configured to receive insulative spacers and retain the spacers in a thickness of the electrode. In other various exemplary embodiments, for example, electrode assemblies in accordance with the present disclosure may include a stainless steel electrode with openings in the electrode body configured to receive insulative spacers and retain the spacers in a thickness of the electrode is contemplated.

Regardless of the materials of construction, exemplary embodiments of an electrode assembly according to the present disclosure include a plurality of insulative spacers that each have a head portion (e.g., a button head) and a body portion that secures to and is retained in a thickness of the electrode. The insulative spacers can be retained in a thickness of an electrode by being fitted or embedded into a respective plurality of openings (e.g., through holes) in an electrode such that at least a portion of the button head of the electrode protrudes or extends slightly beyond the exposed surface of the electrode. Thus, insulative electrode spacers according to various exemplary embodiments of the present disclosure have an advantage over other types of spacers that are adhered or otherwise deposited on the surface on an electrode in that the thickness of the insulative electrode spacers is not limited to the thickness of the desired gap between electrodes. Rather, the insulative electrode spacers according to the present disclosure can have a more robust thickness because at least part of the body and/or head portions of the insulative electrode spacer may be embedded below the exposed surface of the electrode. Accordingly, providing openings in the electrode for the insulative electrode spacers can allow for use of insulative spacers that have a head portion and/or body portion with a robust relative thickness dimension, thereby enhancing the durability of the insulative electrode spacer and overall electrode assembly and making the electrode assembly, including the spacer(s) less susceptible to damage or failure.

Although discussed herein primarily with respect to surgical instrument applications, the present disclosure contemplates that the various electrode spacers and electrode assemblies disclosed herein may be suitable for other applications that utilize opposing electrode assemblies to deliver electrical flux.

With reference now to FIG. 1, a perspective view of a minimally invasive surgical instrument 10 is illustrated. The directions "proximal" and "distal" are used herein to define the directions as shown in FIG. 1, with distal generally being in a direction further along a kinematic arm or closest to the surgical work site in the intended operational use of the instrument 10, for example, in use for performing surgical procedures. As shown in FIG. 1, the instrument 10 generally includes a force/torque drive transmission mechanism 1, an instrument shaft 2 mounted to the transmission mechanism 1, an end effector 3 disposed at the distal end of the instrument 10, and an optional articulation wrist 4 disposed at a distal end of the shaft 2 to support the end effector 3 on the shaft 2.

Figure 6:
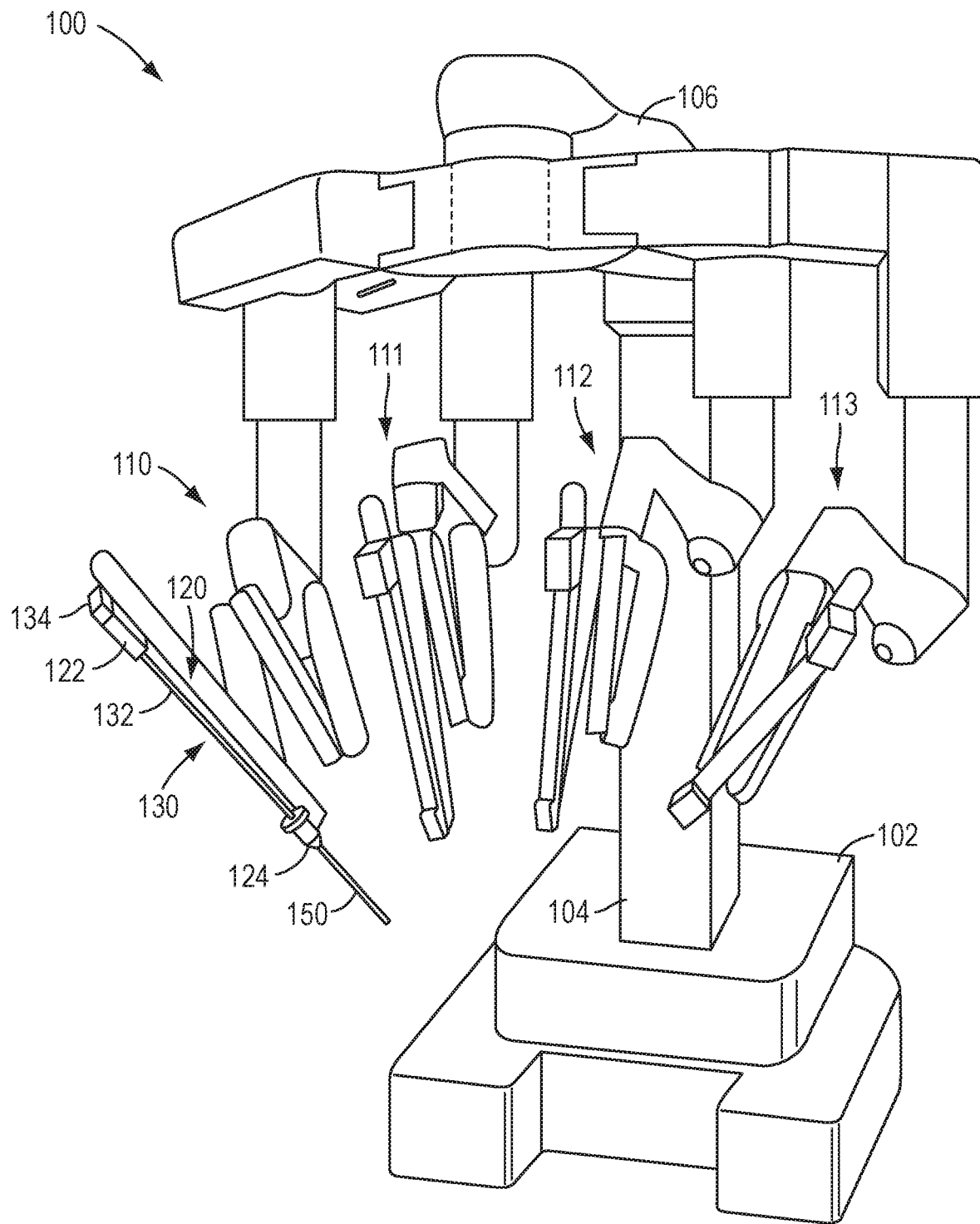
FIG. 6 is a perspective diagrammatic view of a patient side cart in accordance with an exemplary embodiment.

As discussed above, in accordance with various exemplary embodiments, surgical instruments of the present disclosure are configured for use in teleoperated, computer-assisted surgical systems (sometimes referred to as robotic surgical systems). Referring now to FIG. 6, an exemplary embodiment of a patient side cart 100 of a teleoperated, computer-assisted surgical system, to which surgical instruments are configured to be mounted for use, is shown. Such a surgical system may further include a surgeon console (not shown) for receiving input from a user to control instruments of patient side cart 100, as well as an auxiliary control/vision cart (not shown), as described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. Non-limiting, exemplary embodiments of teleoperated, computer-assisted surgical systems with which the principles of the present disclosure may be utilized include the da Vinci® Si Surgical System, Single Site da Vinci® Surgical System, or a da Vinci® Xi Surgical System, available from Intuitive Surgical, Inc. of Sunnyvale, Calif.

Patient side cart 100 includes a base 102, a main column 104, and a main boom 106 connected to main column 104. Patient side cart 100 also includes a plurality of jointed set-up arms 110, 111, 112, 113, which are each connected to main boom 106. Arms 110, 111, 112, 113 each include an instrument mount portion 120 to which an instrument may be mounted, such as instrument 130, which is illustrated as being attached to arm 110. Arms 110, 111, 112, 113 include manipulator portions that can be manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 100 to cause manipulation of an instrument 130 (only one such instrument being mounted in FIG. 1) and/or portions of arm 110 to which the instrument 10 is coupled at the patient side cart 100. Those having ordinary skill in the art would understand that the processor/controller functionality need not be included in an auxiliary/vision cart separate from the patient side cart and surgeon console, but rather could be on a different piece of equipment, on the surgeon console or patient side cart, or distributed between those components.

Instrument mount portion 120 comprises an actuation interface assembly 122 and a cannula mount 124, with a force transmission mechanism 134 of instrument connecting with the actuation interface assembly 122. Cannula mount 124 is configured to hold a cannula 150 through which shaft 132 of instrument 130 may extend to a surgery site during a surgical procedure. Actuation interface assembly 122 contains a variety of drive and other mechanisms that are controlled to respond to input commands at the surgeon console and transmit forces to the force transmission mechanism 134 to actuate instrument 10, as those skilled in the art are familiar with.

Although the exemplary embodiment of FIG. 6 shows an instrument 120 attached to only arm 110 for ease of viewing, an instrument may be attached to any and each of arms 110, 111, 112, 113. An instrument 120 may be a surgical instrument with an end effector, such as instrument 10 as discussed above with reference to FIG. 1. A surgical instrument with an end effector may be attached to and used with any of arms 110, 111, 112, 113. However, the embodiments described herein are not limited to the exemplary embodiment of FIG. 6 and various other teleoperated, computer-assisted surgical system configurations may be used with the exemplary embodiments described herein.

Referring again to FIG. 1, the transmission mechanism 1 transmits received actuation inputs, for example, from a patient side cart in computer-assisted surgical systems or manually, to resulting torques and forces to effect movement of the instrument shaft 2, wrist 4, end effector 3, and/or associated components, to accomplish various motions, potentially resulting in a multiple-degrees-of-freedom (multi-DOF) actuation of the surgical instrument. For example, the transmission mechanism 1 can be controlled via inputs (e.g., torque inputs) to roll shaft 2, and consequently end effector 3 (roll DOF); open and close jaws of the end effector 3 (grip or clamp DOF); articulate wrist 4 (articulation DOF); and translate a cutting element (not shown in the view of FIG. 1) (translation DOF), among others. In various exemplary embodiments, the wrist 4 can be configured for two-DOF articulation in orthogonal directions to provide both "pitch" and "yaw" movement of end effector 3 (yaw being arbitrarily defined as being the plane of motion of the end effector jaws, pitch being orthogonal to yaw).

The transmission mechanism 1 also can accommodate electrical conductors (not shown in FIG. 1) to receive electrosurgical energy via connector 42 that is electrically coupled to an electrical flux generation source (not shown but with which those having ordinary skill in the art have familiarity), that is ultimately transmitted to the end effector 3 and used to deliver an electrosurgical flux, for example to fuse or cauterize tissue. The electrical conductors can be routed from the transmission mechanism 1, down the instrument shaft 2 to the end effector 3.

Additional details regarding exemplary, but non-limiting, embodiments of electrosurgical instruments that include a transmission mechanism and a jawed end effector with opposing electrode assemblies configured for performing fusing and cauterizing (e.g., vessel sealing) are disclosed in U.S. Pat. No. 9,055,961 B2, and being titled "FUSING AND CUTTING SURGICAL INSTRUMENT AND RELATED METHODS," and issued Jun. 16, 2015, which is hereby incorporated by reference herein in its entirety.

Figure 2A:
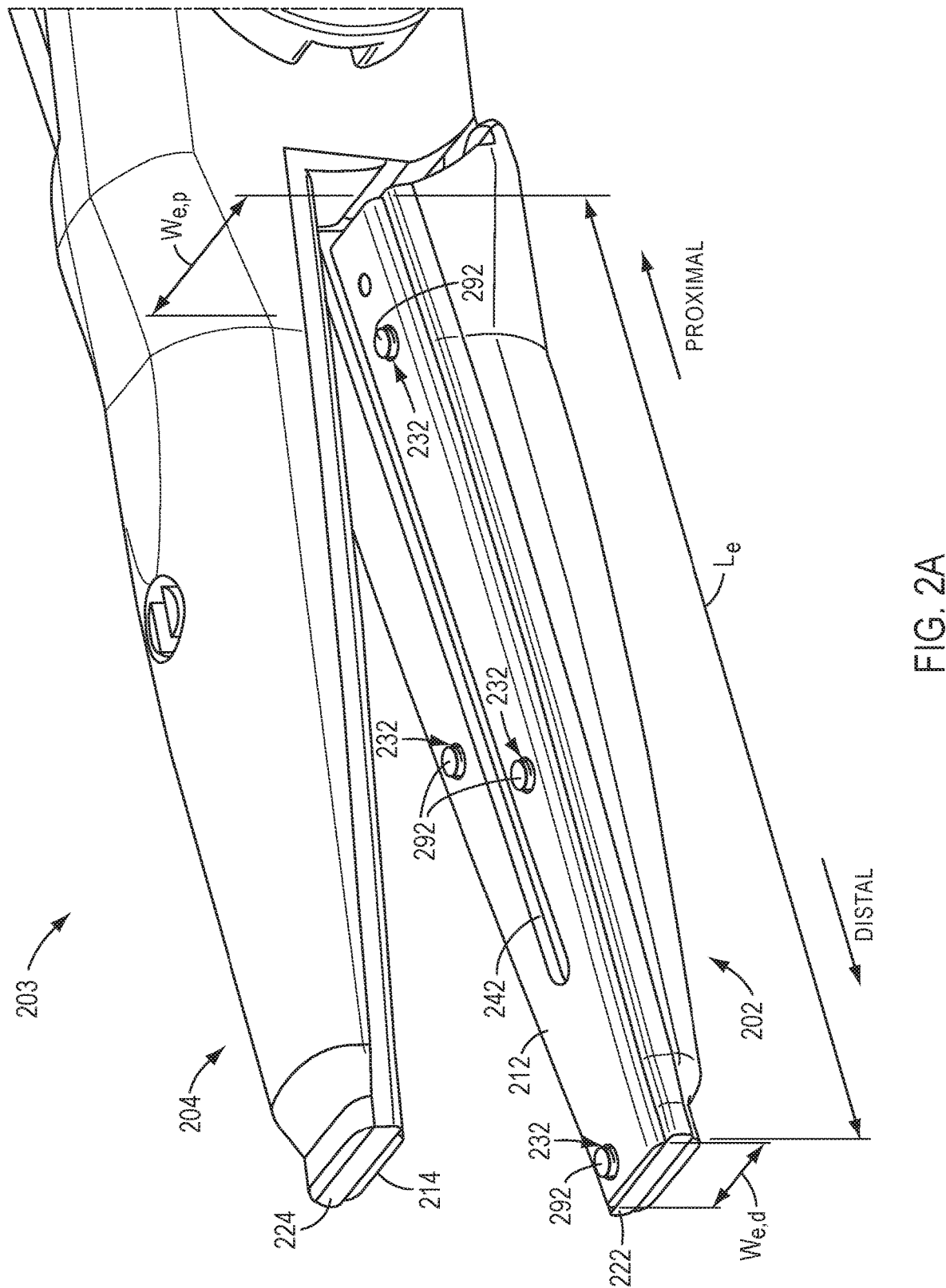
FIG. 2A is a detailed side perspective view of opposing jaw members of an end effector of a surgical instrument in an open position in accordance with an exemplary embodiment.
Figure 2B:
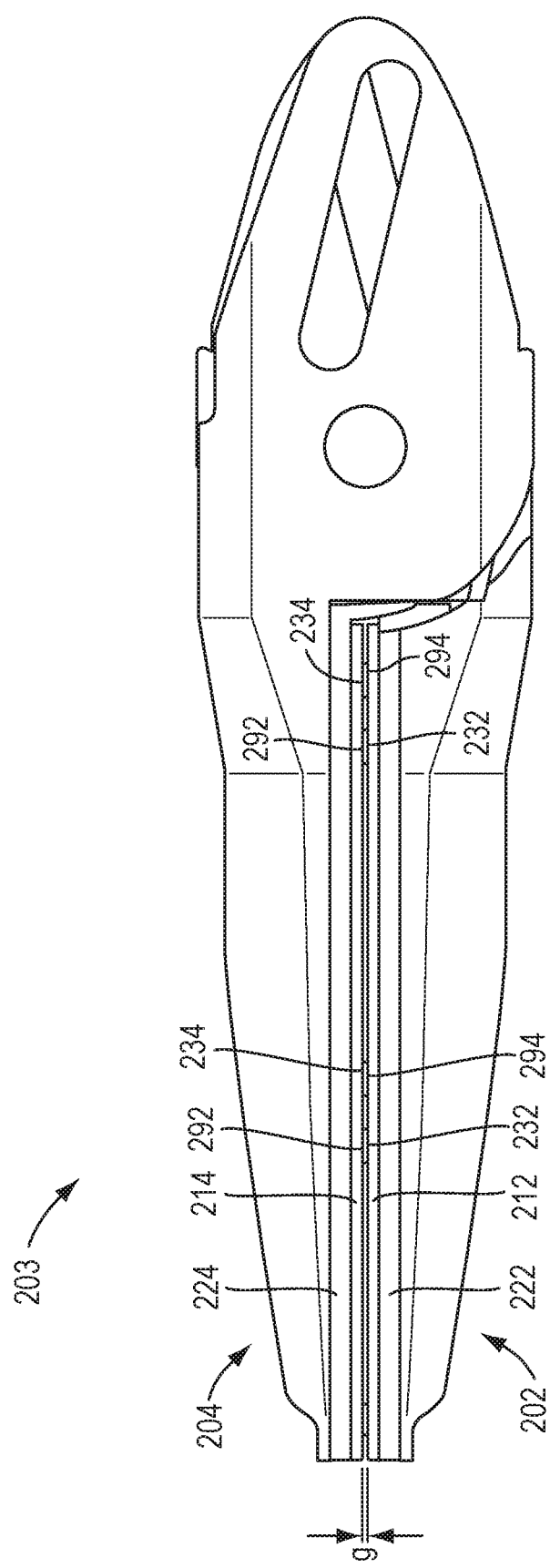
FIG. 2B is a detailed side view of the opposing jaw members of the end effector of FIG. 2A in a closed position.

Turning now to FIGS. 2A and 2B, a detailed side perspective view of an end effector 203 of a surgical instrument, such as, for example the surgical instrument of FIG. 1, is shown. FIG. 2A shows the end effector in an open position and FIG. 2B shows the end effector in a closed position. As shown, the end effector 203 comprises a pair of pivotably coupled opposing jaw members 202, 204. The jaw members 202, 204 extend generally longitudinally and distally from the surgical instrument shaft (not shown in FIG. 2A). At their proximal ends, the jaw members are coupled together to pivot relative to each other between an open position (FIG. 2A) and a closed position (FIG. 2B). The first jaw member 202 supports a first electrode assembly including a first electrode 212, a first electrode support 222, and a first plurality of electrode spacers 232. The second jaw member 204 supports a second electrode assembly including a second electrode 214, a second electrode support 224, and a second plurality of electrode spacers 234 (hidden from view in FIG. 2A).

The length, $L_e$, of each of the electrodes 212, 214 in various exemplary embodiments may range, for example, from about 6 mm to about 40 mm, or from about 16 mm to about 19 mm, which may be desirable for sealing a vessel having a diameter from about 0.1 mm to about 10 mm, or of about 7 mm, although other lengths and diameters may be used depending on the desired application. The width of the electrodes 212, 214, as well as the corresponding jaws members 202, 204, can present a generally tapered shape, for example, having a larger width at the proximal end and a narrower width at the distal end. Such a tapered shape can be beneficial for dissection of tissue, including dissection of vessels. For example, the tapered shape can improve visibility during dissection and can provide a smaller contact area to pierce tissue. In various exemplary embodiments, the width at the proximal end, $W_{e,p}$, ranges from, for example, about 4 mm to about 12 mm, or in some exemplary embodiments, the width $W_{e,p}$ ranges from about 4 mm to about 8 mm; and the width, $W_{e,d}$, at the distal end ranges from, for example, about 1 mm to about 12 mm, or, for another example, the width $W_{e,d}$ may range from about 1 mm to about 8 mm. Such width ranges are exemplary only and more generally the width of the electrodes 212, 214 can be selected based on the desired application, such as, for example, to provide fusing of both sides of dissected tissue (e.g., dissected ends of a vessel) gripped between the jaw members 202, 204. For example, the width may be selected to provide at least about a 1 mm seal on either side of the dissected tissue. The thickness of each electrode 212, 214 in various exemplary embodiments may range from about 0.001 in. to about 0.020 in, or from about 0.005 in. to about 0.015 in., for example, the thickness may be about 0.010 in.

In the exemplary embodiments depicted, such as in FIGS. 2A and 2B, each of the electrodes 212, 214 is provided with a groove 242 (the corresponding groove on electrode 214 is hidden from view in FIG. 2A) configured to receive and provide a track for a cutting blade that translates in the proximal and distal directions relative to the jaw members 202, 204. Similar grooves 342 and 442 are respectively illustrated in the embodiments of FIGS. 3D and 4D, discussed further below. However, in instruments that do not include such a cutting element, the groove in the electrode may be omitted.

With reference to FIG. 2B, in the closed position of the jaw members 202, 204, electrode spacers 232, 234 are provided to maintain the electrodes 212, 214 spaced apart by a gap g. In various exemplary embodiments, the size of the gap g may range from 0.0005 inches to about 0.008 inches, or the size of gap g may range from about 0.001 inches to about 0.007 inches. The insulative electrode spacers 232, 234 are disposed at intervals (which can be uniform or random) along the longitudinal length of each jaw member 202, 204, respectively. Also, insulative electrode spacers 232, 234 may be staggered on top and bottom jaws so that spacers 232 make contact with the surface of electrode 214 and spacers 234 make contact with the surface of electrode 212 in the closed position of the jaw members 202, 204, rather than spacers 232, 234 making contact with each other, Alternatively, although not shown, insulative electrode spacers 232, 234 may be aligned on top and bottom jaws so that spacers 232 make contact with spacers 234 in the closed position of the jaw members 202, 204. In an exemplary embodiment, the height of the electrode spacers 232, 234 above the exposed surface of the electrodes 212, 214 at the proximal portion of the jaw members 202, 204 may be slightly lower than the height of the electrode spacers 232, 234 above the exposed electrode surfaces at the distal portion of the jaw members 202, 204 to promote a uniform gap g across the length of the electrode surfaces while also permitting the electrode surfaces to come sufficiently close along their entire length to ensure effective gripping and sealing of tissue. In various exemplary embodiments, the height of the electrode spacers above the exposed surface of the electrodes ranges from about 0.0005 inches to about 0.008 inches, or from about 0.001 inches to about 0.007 inches.

Advantageously, a working surface 292, 294 of the head portion of each electrode spacer 232, 234 may have a small surface profile relative to the surface profile of the exposed surface of the electrode 212, 214. For example, in some exemplary embodiments, the working surface 292, 294 of each electrode spacer 232, 234 may have a diameter of about 0.635 mm (about 0.025 in.), and surface area of about 0.3 mm$^2$ (about $5 \times 10^{-5}$ in.$^2$). Accordingly, the ratio of the area of the working surface 292, 294 of each electrode spacer 232, 234 to the area of the exposed surface of each electrode may range from about 0.002 to about 0.08.

In addition to maintaining electrodes spaced apart by a gap g, the electrode spacers 232, 234 may also improve the grasping capability of the end effector 203. In various exemplary embodiments, an electrode assembly may include additional electrode spacers beyond what would be required to maintain a gap in order to enhance the grasping ability of an end effector.

By disposing the electrode spacers 232, 234 at intervals along the longitudinal length of each jaw member 202, 204, respectively, and/or providing electrode spacers 232, 234 with working surfaces 292, 294 having a relatively small laterally extending working profile, as described herein, sealing and/or cauterizing can occur over the full length of the electrode assemblies.

Figure 3A:
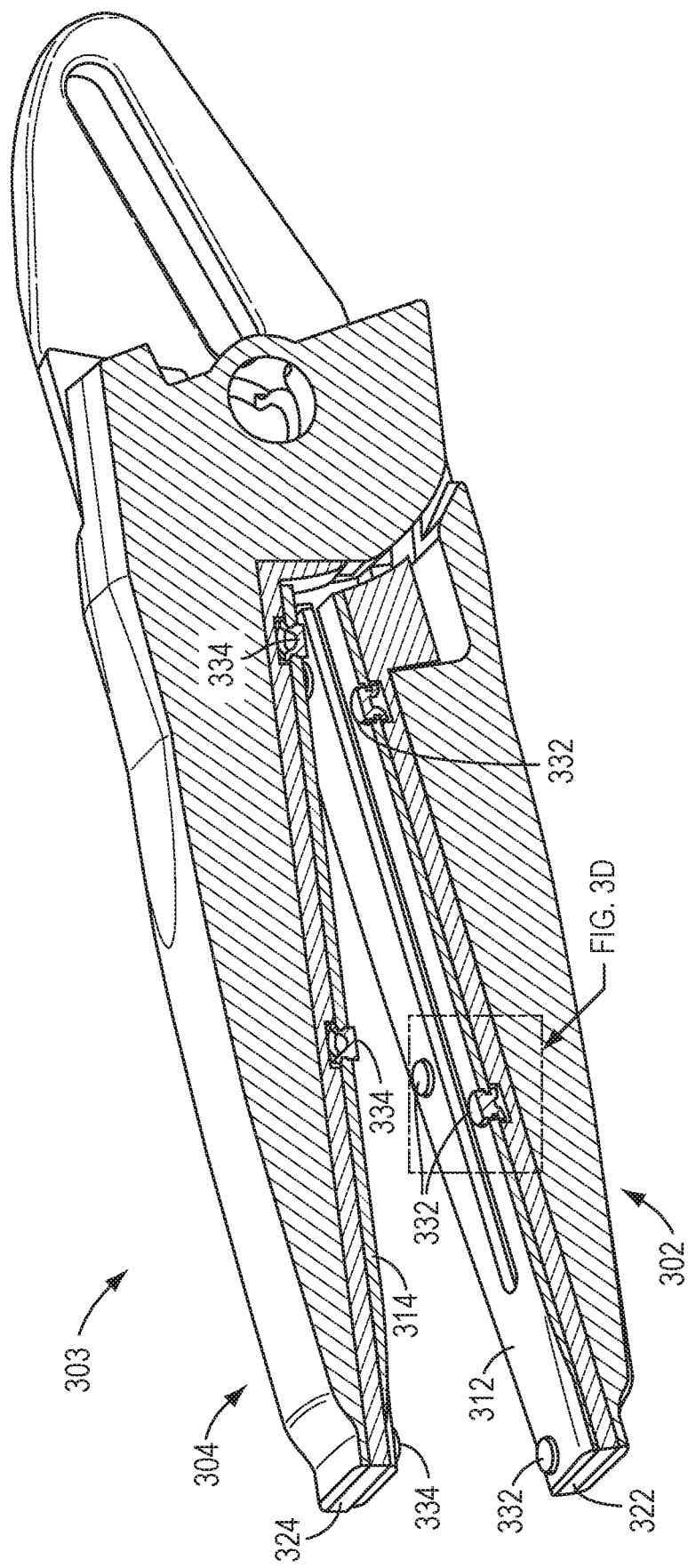
FIG. 3A is a longitudinal cutaway view of a pair of opposing jaw members of an end effector comprising an electrode assembly in accordance with an exemplary embodiment of the present disclosure.

Turning now to FIGS. 3A-3D, various views of an end effector 303 in accordance with an exemplary embodiment are shown. FIG. 3A shows a perspective longitudinal cut-away view of the end effector 303. FIG. 3B is a longitudinal cross-sectional view of the end effector 303 with the jaw members in a closed position, and FIG. 3C is a longitudinal cross-sectional view of the end effector 303 with the jaw members in an open position. As discussed above with reference to FIGS. 2A and 2B, in the closed position of the jaw members 302, 304, electrode spacers 332, 334 are provided to maintain the electrodes 312, 314 spaced apart by a gap g. In various exemplary embodiments, the size of the gap g may range from 0.0005 inches to about 0.008 inches, or the size of gap g may range from about 0.001 inches to about 0.007 inches. The electrode spacers 332, 334 are disposed at intervals along the longitudinal length of each jaw member 302, 304, respectively. In an exemplary embodiment, the height of the electrode spacers 332, 334 above the exposed surface of the electrodes 312, 314 at the proximal portion of the jaw members 302, 304 may be slightly lower than the height of the electrode spacers 332, 334 above the exposed electrode surfaces at the distal portion of the jaw members 302, 304 to promote a uniform gap g across the length of the electrode surfaces while also permitting the electrode surfaces come sufficiently close along their entire length to ensure effective gripping and sealing of tissue.

Figure 3D:
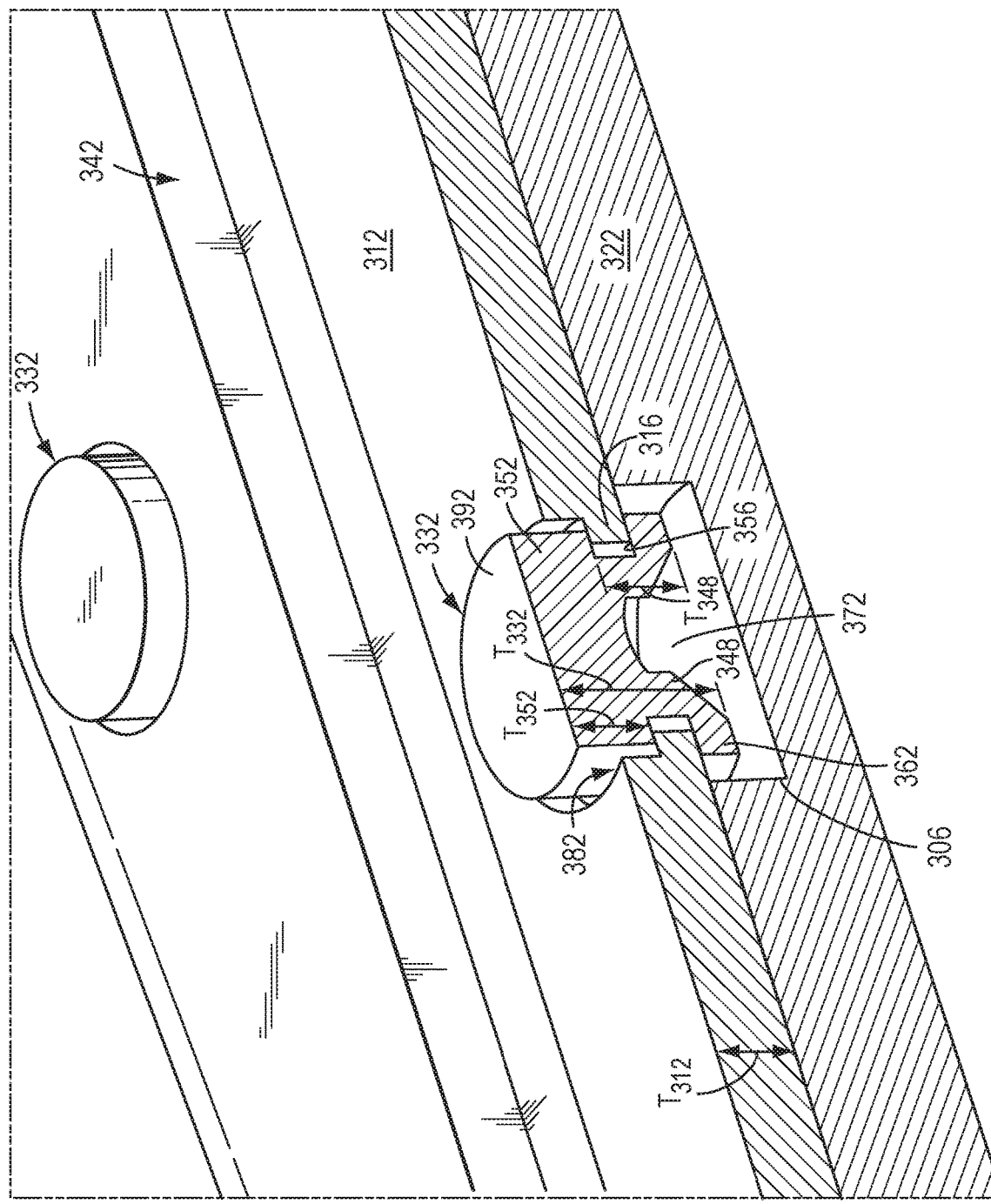
FIG. 3D is a detailed view of the portion labeled FIG. 3D in FIG. 3A.

Details of an individual insulative electrode spacer 332 can be best seen in FIG. 3D, which is a detailed view of the portion labeled FIG. 3D of the jaw member 302 in FIG. 3A. For simplification and ease of description, the configuration of spacers 332, electrode 312, and electrode support 322 of an electrode assembly shown in FIG. 3D is discussed and referred to herein, but one having ordinary skill in the art would appreciate the description applies to the opposing spacers 334, electrode 314, and electrode support 324 of an opposing electrode assembly. Each electrode spacer 332 comprises a head portion 352 that protrudes from the exposed surface of the electrode 312 and a body portion 348 that is retained in a thickness $T_{312}$ of the electrode 312. In exemplary embodiments, the head portion 352 has a button head configuration and the body portion 346 includes a laterally outwardly extending flange 362 extending into the body portion 346. The flange 362 surrounds a recess, such as the chamfered recess 372. The recess 372 can allow for the flange 362 to be resiliently deformed to allow the spacer 332 to be fitted (e.g., swage fit) in an opening 382 (e.g., a through hole) in the electrode 312. To accomplish such a fit, the flange 362 extends past opening 382 and is received in a cavity 306 in the electrode support 322, the opening 382 and cavity 306 being aligned with one another. As perhaps shown best in FIG. 3D, a radial recessed surface 356 of the spacer 332 located between the head 352 portion and the flange 362 is positioned and configured to mate with (receive) a stepped profile 316 of the electrode 312 surrounding the opening 382.

Additionally, although not shown, any other suitable mechanically interlocking mechanisms for fitting the spacers 332, 334 into the respective electrode openings 382, 384 and electrode support cavities 306, 308 are also contemplated. Furthermore, the spacers 332, 334 may be fitted into the respective electrode openings 382, 384 either before or after the electrode 312, 314 has been combined with a respective electrode support 322, 324.

As discussed above, the insulative electrode spacers 332, 334 have a robust thickness because at least part of the head portion 352 and the body portion of the insulative electrode spacer 332 extend into opening 382 and thus are inset below the exposed surface of the electrode 312. Accordingly, providing openings 382 in the electrode 312 for the insulative spacers 332 can allow for use of insulative spacers that have a head and/or body portion with a robust relative thickness, thereby enhancing the durability of the insulative spacer and overall electrode assembly. For example, the head portion 352 can have a thickness $T_{352}$ ranging from about 0.005 in. to about 0.010 in., the body portion 348 can have a thickness $T_{348}$ ranging from about 0.005 in. to about 0.010 in., and the entire insulative spacer 332 can have a thickness $T_{332}$ ranging from about 0.010 in. to about 0.020 in. Thus, compared to the thickness $T_{312}$ of each electrode 312, which may range from about 0.005 in. to about 0.015 in. (e.g., about 0.010 in.), the thicknesses $T_{352}$, $T_{348}$, and $T_{332}$ of the head portion 352, body portion 348, and/or the entire insulative spacer 332, respectively, are relatively robust.

In various exemplary embodiments, an entire electrode spacer 332 made of metal, or at least the entire head portion 352 thereof, or at least a working surface 392 thereof, may be hard anodized such that the spacer is sufficiently insulative. As discussed above, in various exemplary embodiments in accordance with the present disclosure, the hard anodized portion of a metal electrode spacer may have a dielectric strength of at least 200 V/mil (i.e., volts per 0.001 inch). In various other exemplary embodiments in accordance with the present disclosure the hard anodized portion of an electrode spacer may have a dielectric strength of at least 1000 V/mil (i.e., volts per 0.001 inch). In an exemplary method of manufacturing an electrode assembly with a hard anodized spacer, the spacer or a portion thereof is hard anodized before being fitted into the electrode, as described above. Alternatively, in another exemplary method for manufacturing an electrode assembly with a hard anodized spacer, the spacer or a portion thereof is hard anodized after being fitted into the electrode, as described above.

As demonstrated in FIGS. 3A-3D, the electrode support (e.g., electrode support 322, 324) may be separate from the insulative electrode spacers (e.g., 332, 334) thereby allowing for the spacers and electrode supports to be made from different materials without increasing the complexity of manufacturing the electrode assembly. It may be advantageous to be able to make the electrode support from a different material than the material that the insulative electrode spacers are made from because it may be sufficient to make the electrode support from a less durable material than the spacer in view of the positioning, configuration, and use of the electrode support not being as prone to damage. Being able to make the support out of a less durable material can in turn reduce overall manufacturing costs of electrode assemblies in accordance with various exemplary embodiments of the present disclosure. Accordingly, in various exemplary embodiments, the electrode supports (e.g., 322, 324) may be made of lower strength insulative material such as, for example, plastic and ceramic.

Figure 4A:
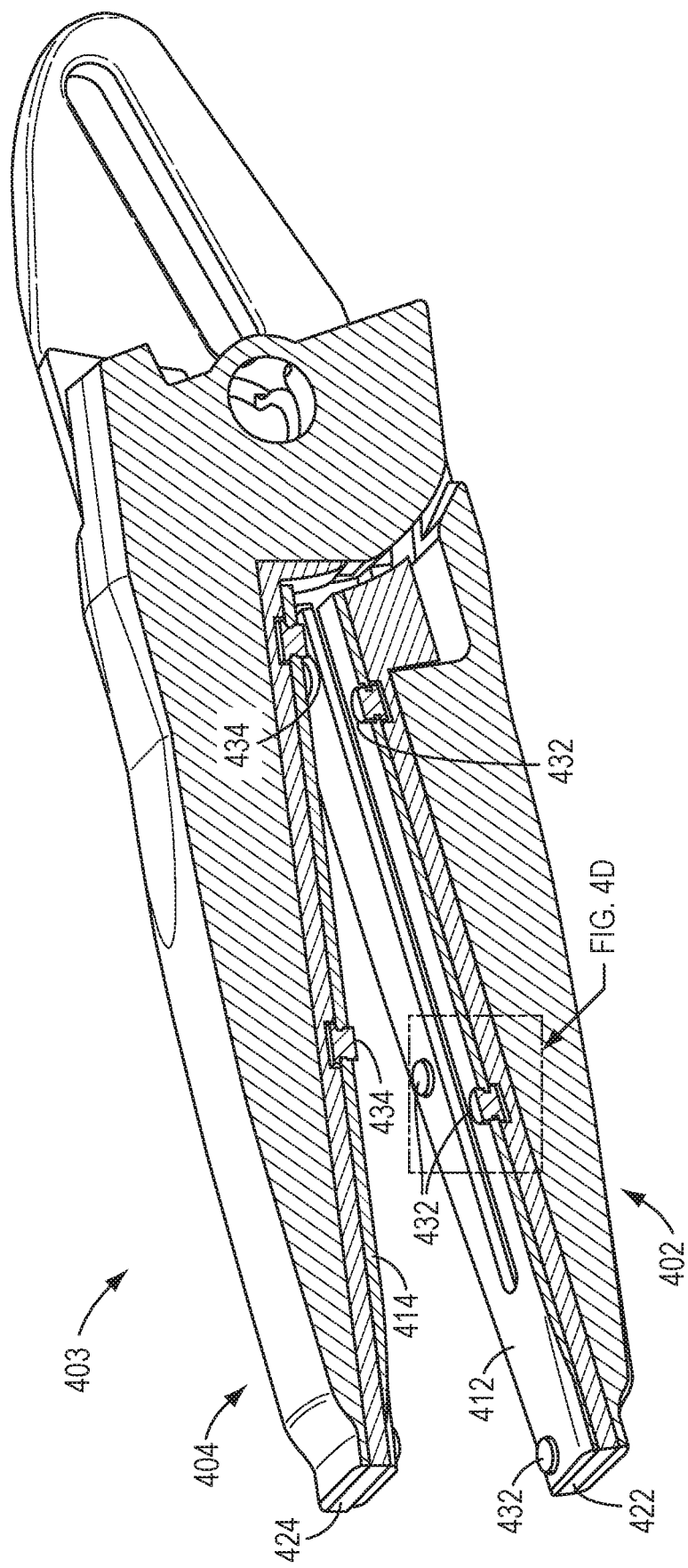
FIG. 4A is a longitudinal cutaway view of a pair of opposing jaw members of an end effector comprising an electrode assembly in accordance with an exemplary embodiment of the present disclosure.
Figure 4B:
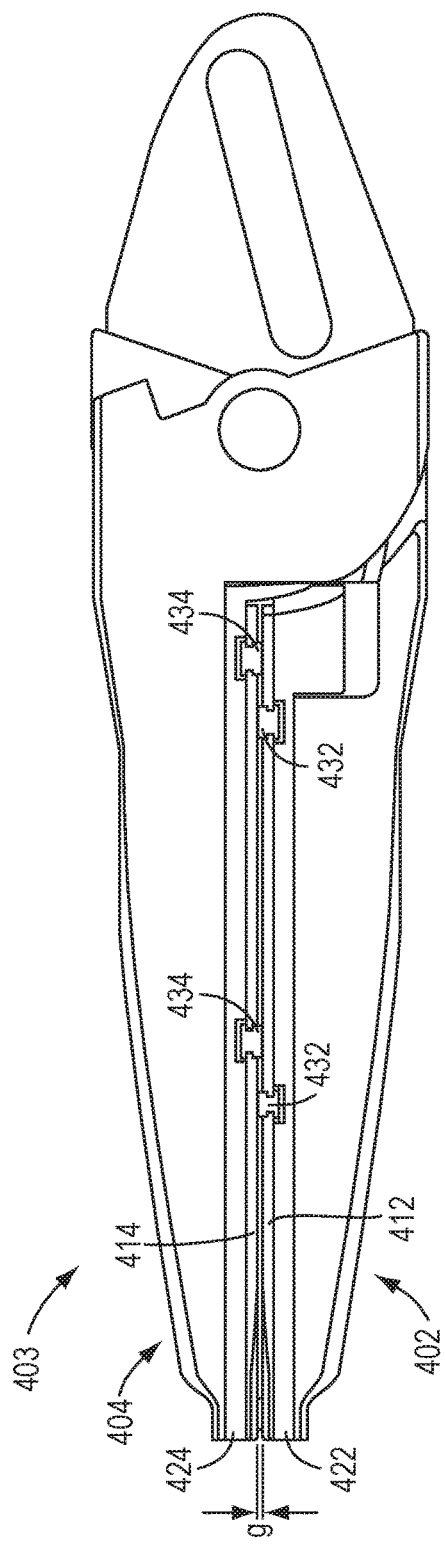
FIG. 4B is a longitudinal cross-sectional view of the end effector of FIG. 4A with the jaw members in a closed position.
Figure 4C:
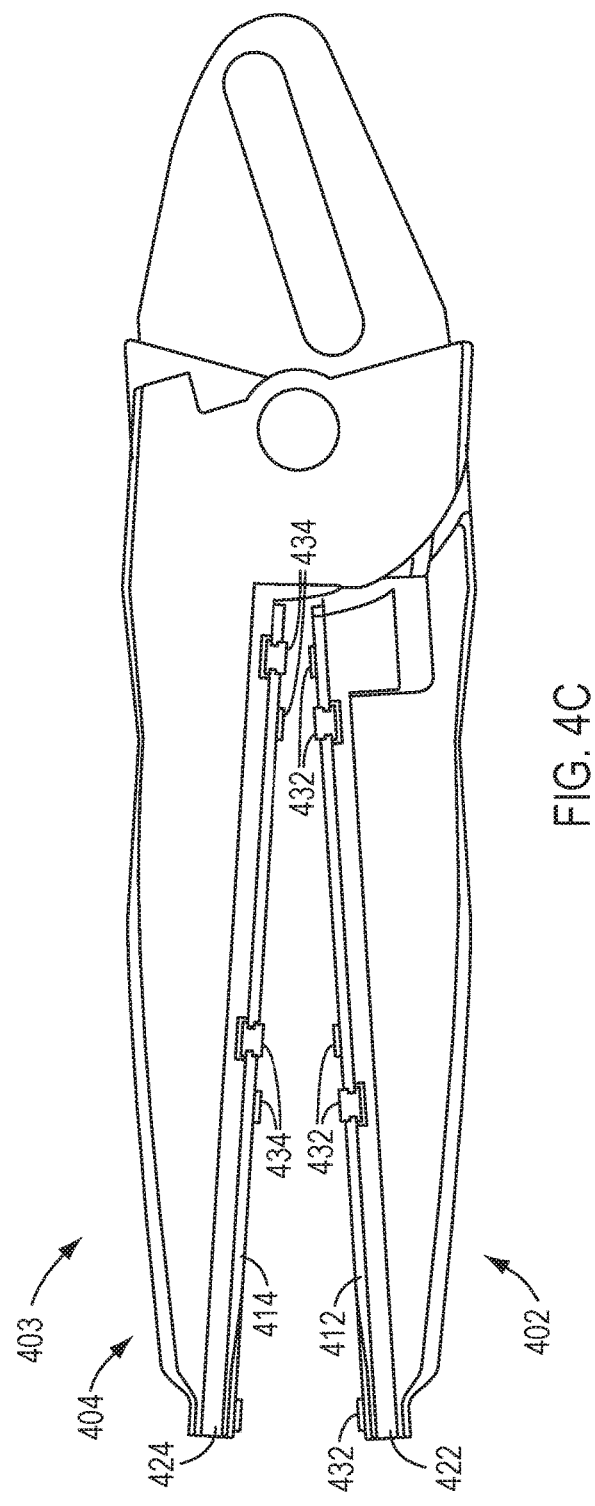
FIG. 4C is a longitudinal cross-sectional view of the end effector of FIG. 4A with the jaw members in an open position.

Turning now to FIGS. 4A-4D various views of an end effector 403 in accordance with an exemplary embodiment are shown. FIG. 4A shows a perspective longitudinal cutaway view of the end effector 403. FIG. 4B is a longitudinal cross-sectional view of the end effector 403 with the jaw members 402, 404 in a closed position, and FIG. 4C is a longitudinal cross-sectional view of the end effector 303 with the jaw members 402, 404 in an open position.

As with the exemplary embodiments of FIGS. 2A-2B and 3A-3D, in the closed position of the jaw members 402, 404, the electrodes 412, 414 of FIGS. 4A-4D are maintained spaced apart by a gap g using electrode spacers 432, 434 disposed at intervals (which can be uniform or random) along the longitudinal length of each jaw member 402, 404, respectively. In various exemplary embodiments, the size of the gap g ranges from about 0.0005 inches to about 0.008 inches, or from about 0.001 inches to about 0.007 inches. Also, in various exemplary embodiments, the height of the electrode spacers above the exposed surface of the electrodes ranges from about 0.0005 inches to about 0.008 inches, or from about 0.001 inches to about 0.007 inches.

Figure 4D:
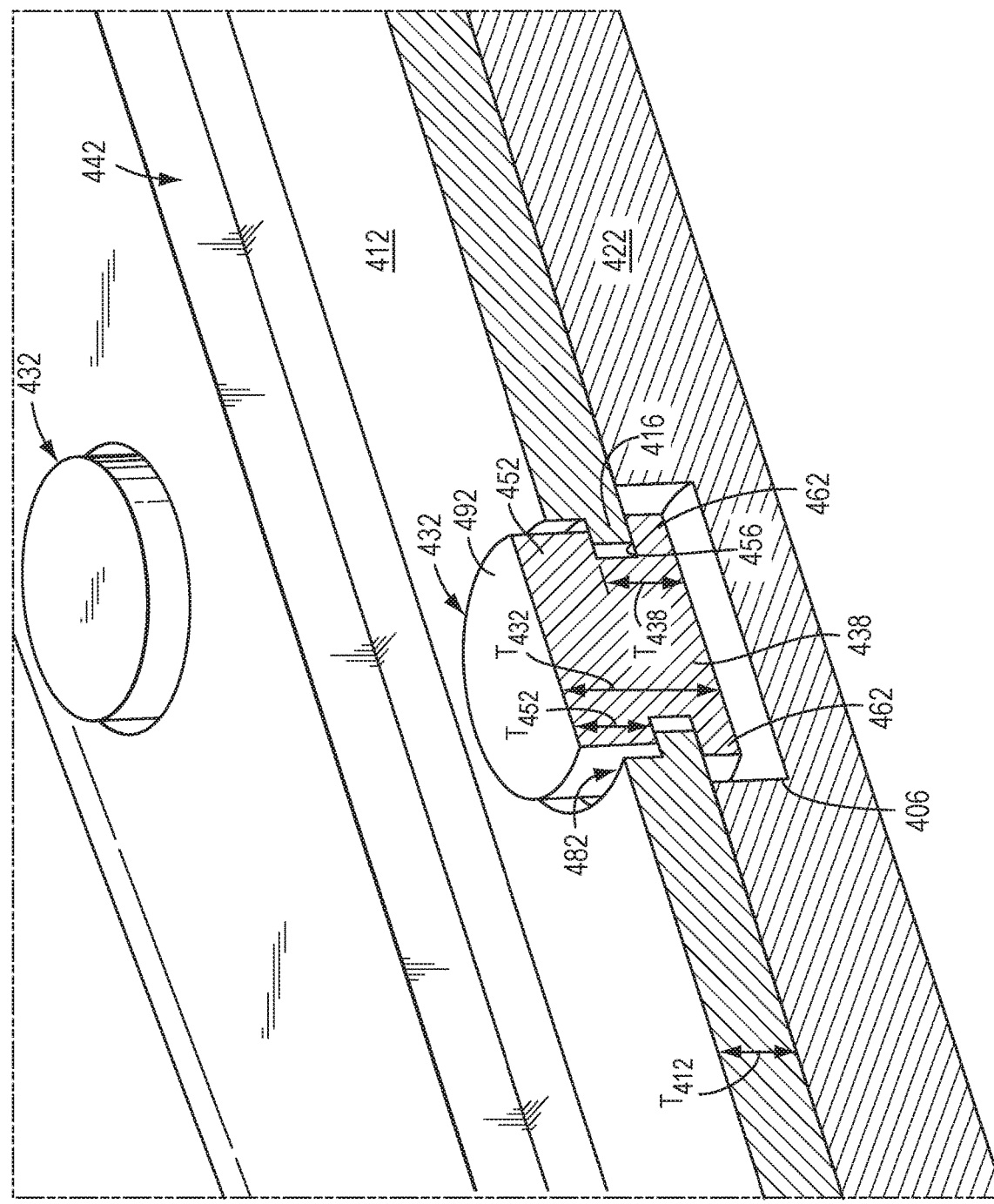
FIG. 4D is a detailed side view of the portion labeled FIG. 4D on FIG. 4A.

As can be best seen in FIG. 4D, which is a detailed side view of the portion labeled FIG. 4D of the jaw member 402, each electrode spacer 432, 434 comprises a head portion 452 that protrudes from the exposed surface of the electrode 412 and a body portion 438 that secures to the electrode 412. In exemplary embodiments, the head portion 452 has a button head configuration including a working surface 492 and the body portion 438 has a laterally outwardly extending flange 462. In some exemplary embodiments, such as, for example, jaw member 402, the body portion 438 has a flat, solid bottom forming the flange 462 rather than a recess (e.g., recess 372 in FIG. 3D). Having a solid body portion with a flat solid disk-shaped) bottom forming the flange 462 makes the lateral sides of the insulative electrode spacer 432 more resistant to the forces imposed thereupon by the electrode 412 made of a metal injection molded material during a sintering process, as will be further described below with reference to the exemplary embodiments of FIGS. 5A and 5B. Accordingly, the insulative electrode spacer 432 having a solid body portion 438 with a disk-shaped bottom may be less susceptible to deformation during sintering of a metal injection molded electrode 412. Although a relatively flat profiled, disk-shaped bottom is illustrated, those having ordinary skill in the art would understand that other configurations may be employed and are considered within the scope of the present disclosure, though it is generally desirable to minimize the dimensions while provided a retaining surface (flange) configured to interact with the electrode to retain the spacer in position while also providing a relatively increased thickness of the spacer as discussed herein.

In the assembled electrode assembly shown in FIGS. 4A-4D, as can best be seen in FIG. 4D, the flange 462 is received through the opening 482 and into a cavity 406 in the electrode support 422, the opening 482 and cavity 406 being aligned with one another, and a radial recess 456 between the head 452 portion and the flange 462 receives a stepped profile 416 of the electrode 412. One having ordinary skill in the art would appreciate that the opposing spacers 434, opposing electrode 414, and corresponding electrode support 424 have a similar configuration as that described above.

Additionally, although not shown, any other suitable mechanically interlocking mechanisms for embedding the insulative spacers 432, 434 into the respective electrode openings 482, 484 and electrode support cavities 406, 408 are also contemplated.

As discussed above, the insulative electrode spacer 432 is able to have a robust thickness because at least part of the insulative electrode spacer 432 (e.g., at least a portion of the body portion and optionally a portion of the head portion) extend into a thickness of the electrode, for example by being fit into opening 482 and thus inset below the exposed surface of the electrode 412. Accordingly, providing openings 482 in a thickness $T_{412}$ of the electrode 412 that are configured to receive the insulative spacers 432 can allow for use of insulative spacers that have a head and/or body portion with a robust relative thickness, thereby enhancing the durability of the insulative spacer and overall electrode assembly. For example, the head portion 452 can have a thickness $T_{452}$ ranging from about 0.005 in. to about 0.010 in., the body portion 438 can have a thickness $T_{438}$ ranging from about 0.005 in. to about 0.010 in., and the entire insulative spacer 432 can have a thickness $T_{432}$ ranging from about 0.010 in. to about 0.020 in. Thus, compared to the thickness $T_{412}$ of each electrode 412, which may range from about 0.005 in. to about 0.015 in. (e.g., about 0.010 in.), the thicknesses $T_{452}$, $T_{438}$ and $T_{432}$ of the head portion 452, body portion 438, and/or the entire insulative spacer 432, respectively, are relatively robust.

In the exemplary embodiment of FIGS. 4A-4D, the electrode spacers 432, 434 may be made of a ceramic, such as, for example zirconium oxide, aluminum oxide, titanium oxide, or combinations thereof, or a hard anodized metal, such as, for example aluminum, zirconium, titanium, magnesium, or alloys thereof. Furthermore, in combination with ceramic insulative electrode spacers 432, 434, the electrodes 412, 414 may be made from metal, including but not limited to, for example, a metal injection molded material.

Figure 5A:
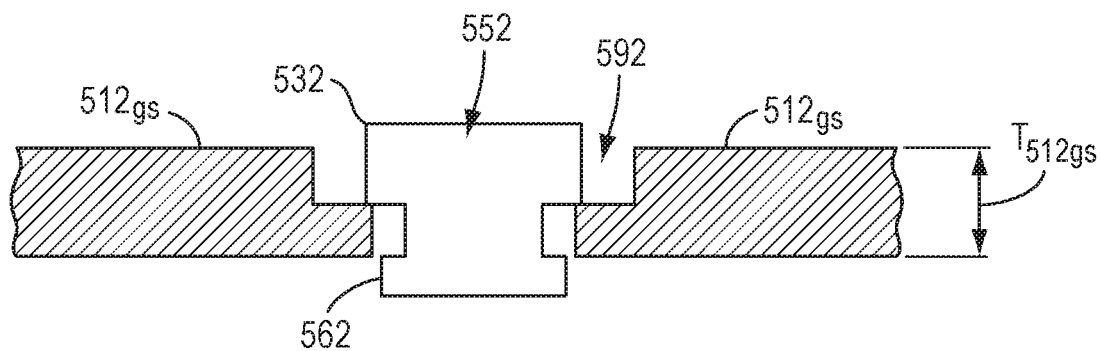
FIG. 5A is a detailed cross-sectional view of an electrode assembly in an unsintered state of the electrode during manufacture of the electrode assembly in accordance with the present disclosure.
Figure 5B:
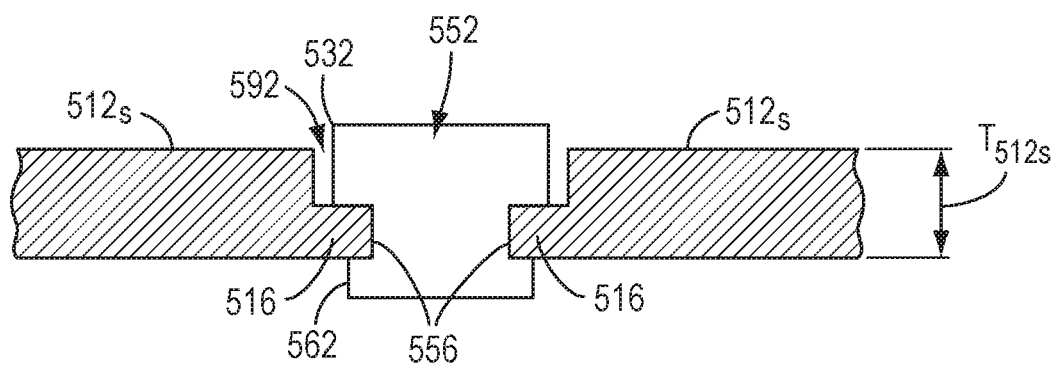
FIG. 5B is a detailed cross-sectional view of an electrode assembly in a sintered state of the electrode during manufacture of the electrode assembly in accordance with the present disclosure.

Illustrations of an exemplary embodiment of a process of incorporating an insulative electrode spacer 532 into a thickness of an electrode are shown in FIGS. 5A and 5B. The electrode 512 is made of metal injection molded (MIM) material formed from, for example, a binder plus powdered stainless steel, zirconium, titanium, or combinations thereof. First, as shown in FIG. 5A, an electrode spacer 532 is disposed within an opening 592 within a MIM electrode $512_{gs}$ (having a thickness $T_{512gs}$) that is in a "green state" (i.e., unsintered), such that the underside of the button head 552 rests upon the portion of the exposed surface of the unsintered MIM electrode $512_{gs}$ that surround the opening 592.

FIG. 5B shows the electrode assembly after the MIM electrode $512_s$ has been sintered. Sintering causes the opening 592 to shrink such that the stepped perimeter walls surrounding the opening 592 of the sintered electrode $512_s$ fit against the lateral walls of the electrode spacer 532, and between the button head 552 and the flange 562 such that stepped profile 516 mates with radial recess 556, thereby retaining (fixing) the electrode spacer 532 in a thickness $T_{512s}$ of the electrode to maintain the spacer 532 in place relative to the electrode $512_s$.

A ceramic or other suitably high melting point material that is relatively durable is used as the material of the spacer 532 in the embodiment of FIGS. 5A-5B, so that the spacer 532 is not deformed or otherwise affected by the sintering process. By virtue of its inherent durability, ceramic spacers are more resistant to the forces imposed thereupon by a MIM electrode 512 during a sintering process, as described above.

After insulative electrode spacers 532 have been embedded in a thickness of the sintered electrode $512_s$, the combined structure may then be overlaid and affixed to (or otherwise combined with) a corresponding electrode support (omitted for clarity from FIGS. 5A and 5B). Alternatively, if the electrode support is made from a sufficiently high melting point material, each electrode spacer 532 may be disposed within an opening 592 within a MIM electrode $512_{gs}$ that is in a "green state" (i.e., unsintered), and a corresponding cavity (similar to cavities 306 and 406 of FIGS. 3 and 4) of the electrode support such that the electrode $512_{gs}$ is overlaid on the electrode support prior to being sintered. Then, the electrode may be sintered so as to retain (fix) the electrode spacer 532 in a thickness $T_{512s}$ of the electrode. Furthermore the sintering may sufficiently shrink the electrode $512_s$ so that is becomes fitted or affixed to the electrode support.

Aside from the hard anodization for the spacers described above, other processes to enhance dielectric properties of an anodized coating that can be utilized in exemplary embodiments of the present disclosure. For example, the anodizing processes commercially available from Tiodize® Co. Inc. may be used to achieve the desired dielectric and durability properties of the electrode spacers contemplated in the present disclosure.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

The nature of information depicted in the figures and described herein is exemplary. Those persons having skilled in the art would appreciate modifications to the electrode spacers and electrode assemblies can be made, such as for example, modifications to structure, dimensions, materials, and methodologies may be made without departing from the scope of the present disclosure.

It is to be understood that the particular examples and embodiments set forth herein are nonlimiting, and modifications to structure, dimensions, materials, and methodologies may be made without departing from the scope of the present disclosure and claims including equivalents.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents.

What is claimed is:

1. An electrode assembly comprising:
   an electrode support made of a first electrically insulative material;
   an electrode on the electrode support, the electrode having a working surface extending generally transverse to a thickness of the electrode; and
   a plurality of insulative spacers retained in the electrode and made of a second electrically insulative material, the second electrically insulative material being different from the first electrically insulative material,
   wherein each insulative spacer comprises:
      a body portion extending into the thickness of the electrode,
      a flange extending laterally outward from the body portion,
      a head portion protruding beyond the working surface of the electrode; and
      a recessed region defined around a perimeter of the body portion between the head portion and the flange,
   wherein the electrode comprises a stepped profile around each insulative spacer, a portion of the stepped profile being received by the recessed region.

2. The electrode assembly of claim 1, wherein the plurality of insulative spacers are swage fitted, press fitted, or sinter fitted respectively into a plurality of openings in the electrode.

3. The electrode assembly of claim 1, wherein the second electrically insulative material is chosen from metal and ceramic.

4. The electrode assembly of claim 1, wherein the electrode comprises stainless steel, zirconium, and/or titanium.

5. The electrode assembly of claim 1, wherein the first electrically insulative material is plastic or ceramic.

6. The electrode assembly of claim 1, wherein at least a portion of each electrically insulative spacer is hard anodized.

7. The electrode assembly of claim 6, wherein at least the portion of each electrically insulative spacer that is hard anodized has a dielectric strength of at least 200 V/mil.

8. The electrode assembly of claim 6, wherein at least the portion of each electrically insulative spacer that is hard anodized has a dielectric strength of at least 1000 V/mil.

9. The electrode assembly of claim 1, wherein the body portion of each electrically insulative spacer further comprises a chamfered recess surrounded by the laterally outwardly extending flange.

10. A method for making an electrode assembly, comprising:
    providing an electrode with a plurality of openings extending into a thickness of the electrode, the electrode having a stepped profile surrounding each opening;
    inserting a plurality of electrically insulative spacers in the plurality of openings, respectively, wherein each electrically insulative spacer comprises a body portion, a flange extending laterally outward from the body portion, a head portion, and a recessed region defined around a perimeter of the body portion between the head portion and the flange, wherein at least part of the body portion of each electrically insulative spacer is positioned in each opening such that the stepped profile surrounding the opening is received by the recessed region and the head portion of each electrically insulative spacer is positioned to protrude beyond an exposed working surface of the electrode, and wherein each electrically insulative spacer is made of metal or ceramic; and
    retaining each inserted electrically insulative spacer in each opening by engagement of the flange of each electrically insulative spacer with the electrode.

11. The method of claim 10, wherein the flange is elastically deformed during the inserting of each electrically insulative spacer in each opening.

12. The method of claim 10, wherein the electrode is a metal injection molded electrode and the inserting occurs during an unsintered state of the electrode.

13. The method of claim 12, further comprising, after the inserting,
    sintering the electrode to shrink the opening of the electrode, the shrinking causing the retaining of each insulative spacer in each opening.

14. The method of claim 10, further comprising hard anodizing at least part of the head portion of each electrically insulative spacer.

15. The method of claim 10, further comprising receiving a portion of the body portion of each electrically insulative spacer in a cavity of an electrode support.

16. The method of claim 15, wherein the electrode support is made of a different material than the plurality of electrically insulative spacers.

17. An electrosurgical instrument, comprising:
    a shaft;
    an end effector operably coupled to the shaft, the end effector comprising a pair of opposing jaw members, each jaw member comprising an electrode assembly disposed to face the electrode assembly of the opposing jaw member, the electrode assembly comprising:
    an electrode support made of a first electrically insulative material;

an electrode on the electrode support, the electrode having a working surface extending generally transverse to a thickness of the electrode; and a plurality of insulative spacers retained in the electrode and made of a second electrically insulative material, the second electrically insulative material being different from the first electrically insulative material, each insulative spacer comprising:

a body portion extending into the thickness of the electrode, a flange extending laterally outward from the body portion, a head portion protruding beyond the working surface of the electrode; and a recessed region defined around a perimeter of the body portion between the head portion and the flange, wherein the electrode comprises a stepped profile around each insulative spacer, a portion of the stepped profile being received by the recessed region.

18. The electrode assembly of claim 17, wherein the second electrically insulative material is chosen from metal and ceramic.

19. The electrode assembly of claim 17, wherein the electrode comprises stainless steel, zirconium, and/or titanium.

20. The electrode assembly of claim 17, wherein the first electrically insulative material is plastic.

21. The electrode assembly of claim 17, wherein at least a portion of each electrically insulative spacer is hard anodized.

* * * * *